(12) United States Patent
Hoftman et al.

(10) Patent No.: US 8,596,453 A0
(45) Date of Patent: Dec. 3, 2013

(54) SCALPEL BLADE REMOVER AND SHARPS CONTAINER

(76) Inventors: Mike Hoftman, Calabasas, CA (US); William Baer, Simi Valley, CA (US)

(*) Notice: Subject to any disclaimer, the term of this patent is extended or adjusted under 35 U.S.C. 154(b) by 0 days.

(21) Appl. No.: 10/706,353

(22) Filed: Nov. 12, 2003

(65) Prior Publication Data

US 2004/0111853 A1 Jun. 17, 2004

Related U.S. Application Data

(63) Continuation-in-part of application No. 60/425,866, filed on Nov. 12, 2002.

(51) Int. Cl.
B65D 85/10 (2006.01)
B23P 19/02 (2006.01)

(52) U.S. Cl.
USPC ............... 206/355; 206/359; 29/239; 29/278; 30/339

(58) Field of Classification Search
USPC ............ 206/355, 359, 363, 370; 29/239, 278; 30/339; 606/167
See application file for complete search history.

(56) References Cited

U.S. PATENT DOCUMENTS

| | | | |
|---|---|---|---|
| 4,106,620 A * | 8/1978 | Brimmer et al. | |
| 4,318,473 A | 3/1982 | Sandel | |
| 4,344,532 A * | 8/1982 | Eldridge et al. | |
| 4,395,807 A * | 8/1983 | Eldridge et al. | |
| 4,746,016 A * | 5/1988 | Pollak et al. | |
| 4,903,390 A * | 2/1990 | Vidal et al. | |
| 5,088,173 A * | 2/1992 | Kromer et al. | |
| 5,361,902 A * | 11/1994 | Abidin et al. | |
| 5,449,068 A * | 9/1995 | Gharibian | |
| 5,729,879 A | 3/1998 | Hoftman | |
| 5,875,532 A * | 3/1999 | Musgrave et al. | |
| 5,875,533 A * | 3/1999 | Henry | |

* cited by examiner

Primary Examiner — Jila M. Mohandesi
(74) Attorney, Agent, or Firm — David T. Bracken

(57) ABSTRACT

The present invention is a scalpel blade removal device comprising an opening in a wall defining a first blade guide, extending to a narrowing upward ramp bounded by left and right guide walls. A horizontal top ramp extends from the distal end of the upward ramp, bounded by left and right guide towers. A spring loaded notch device is adapted to lock behind a proximal end of a scalpel blade seated on a scalpel, where the scalpel is inserted in the opening and the blade edge is driven up the ramp to the top ramp. When the notch device is locked behind that end of the scalpel blade, the scalpel is pulled back, causing the scalpel blade to slide off the scalpel handle. A sharps container incorporates the removal device, a reinforced latch, a scalpel resting location, and needle cover removers.

11 Claims, 5 Drawing Sheets

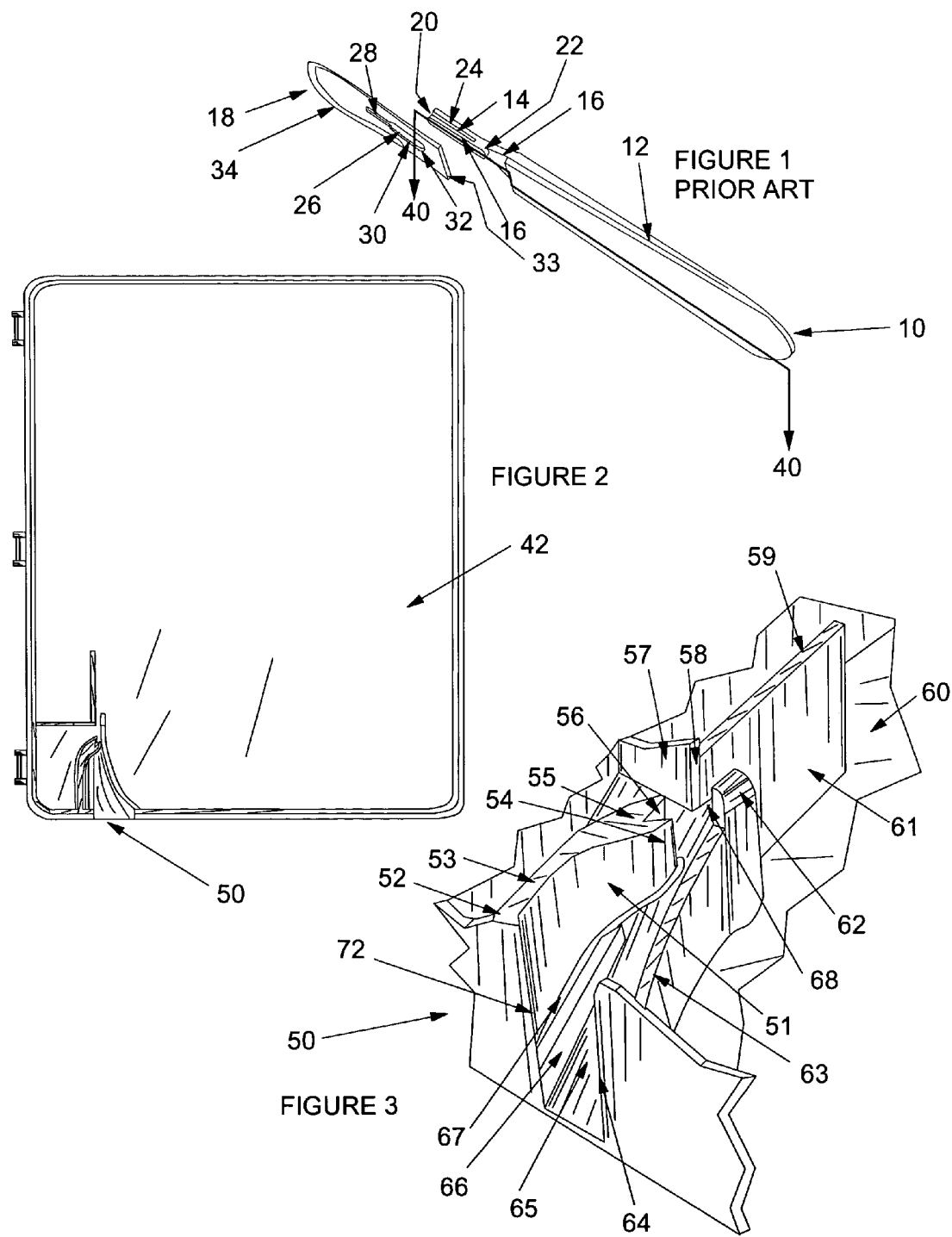

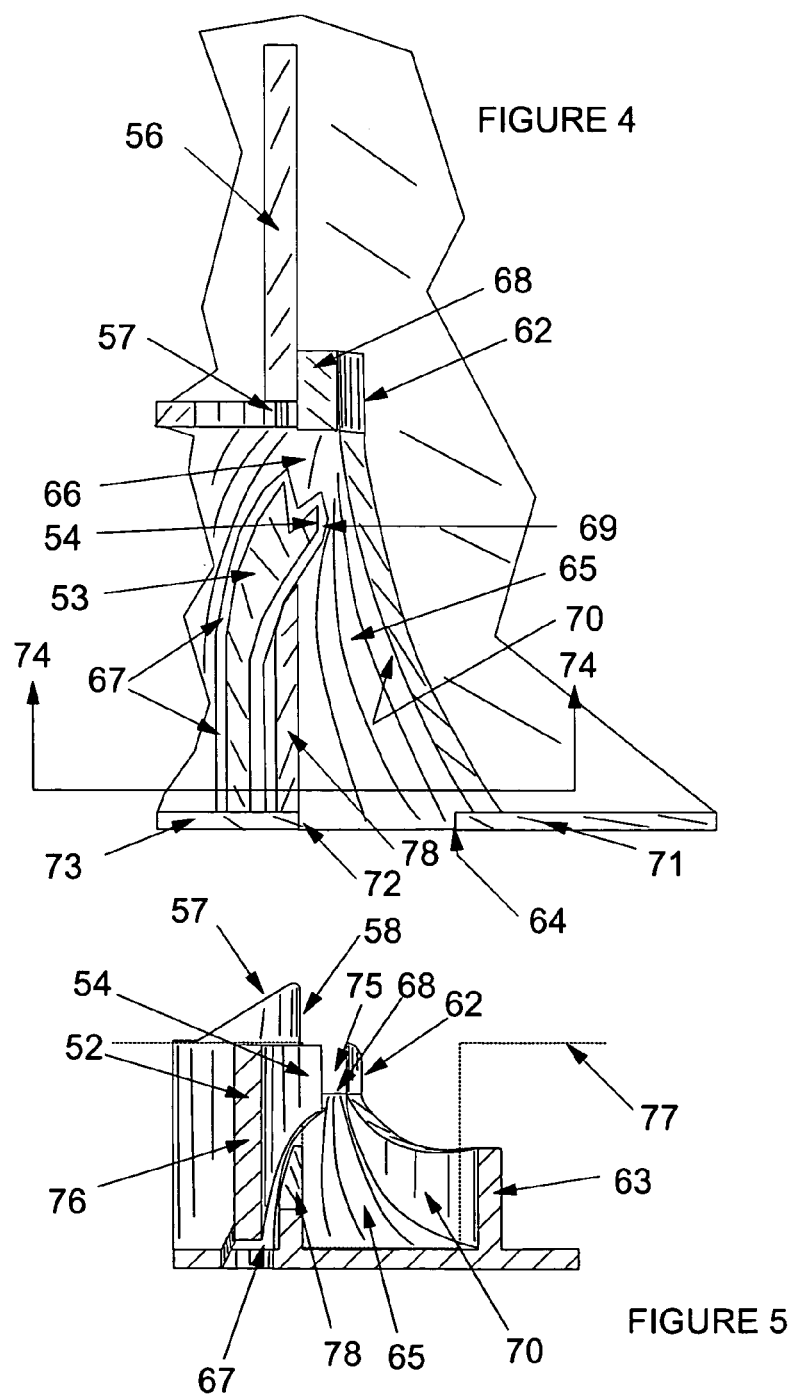

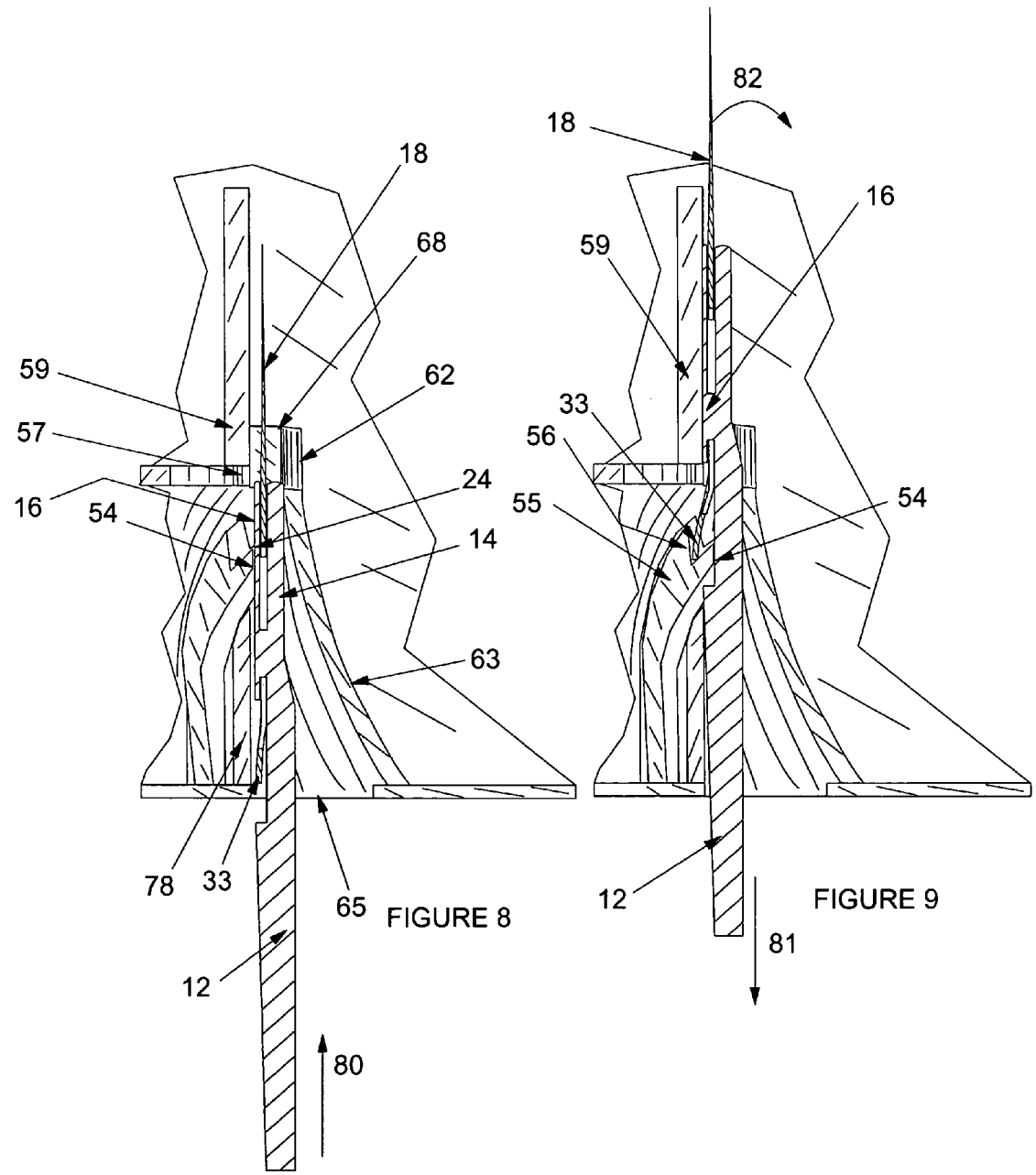

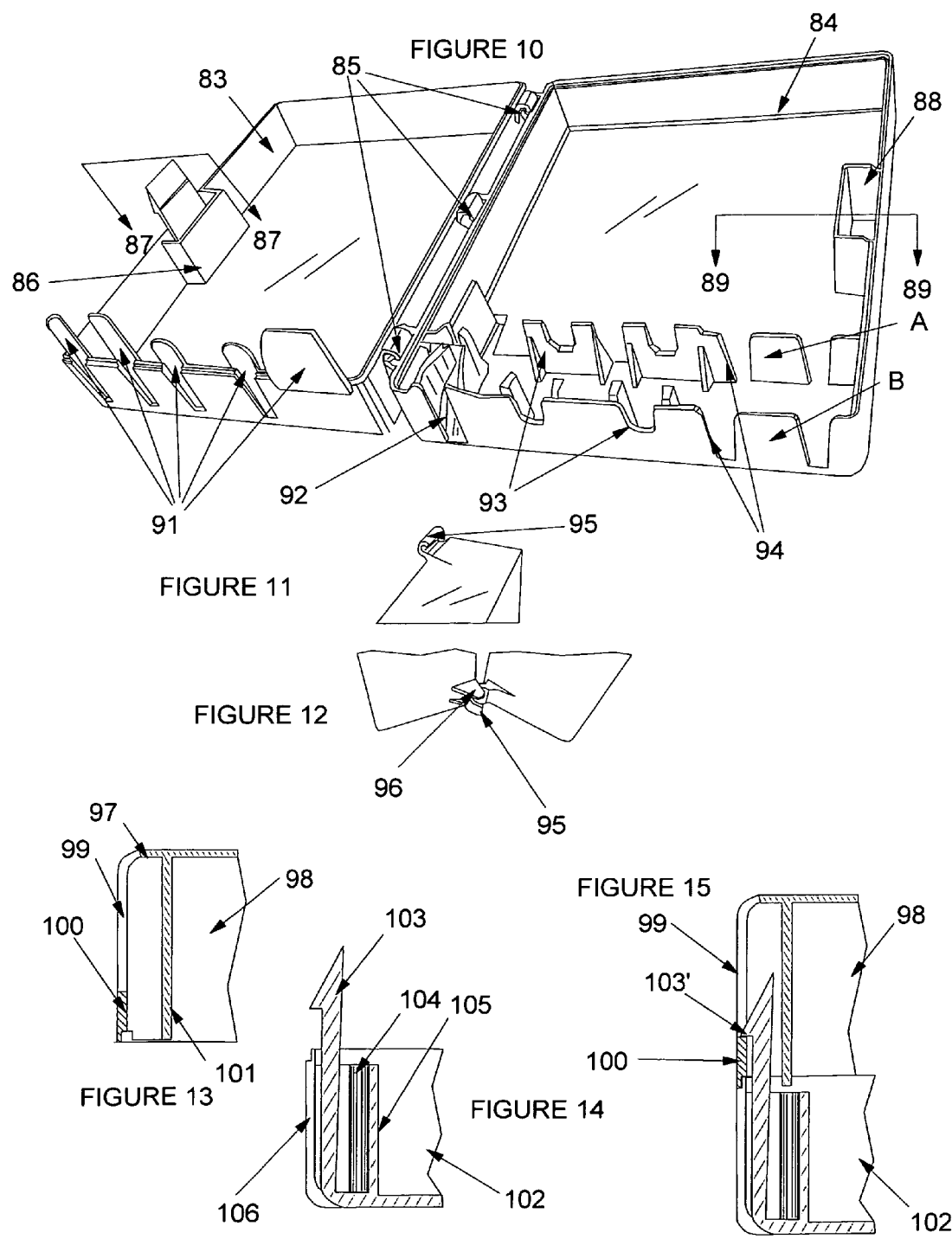

SCALPEL BLADE REMOVER AND SHARPS CONTAINER

This application is a continuation in part of Ser. No. 60/425,866 filed Nov. 12, 2002.

BACKGROUND OF THE INVENTION

The present invention relates to the removal of blades from scalpel handles.

During or at the end of a surgical procedure, disposable scalpel blade must be removed from non-disposable scalpel handles. During surgery, some of the disposable blades may get dull or become contaminated and must be replaced by new sharp, sterile blades.

A prior art scalpel handle 10 is shown in FIG. 1 and has a handle portion 12 and a narrow inserted portion 14 connected by a neck portion 16. The inserted portion 14 is located at the forward end of the handle 10 and is adapted to hold a blade 18. The inserted portion 14 has a rounded front end 20 and a rounded rear end 22 with grooves 24 provided around the outer periphery. The blade 18 has a keyed slot 26 with a narrow portion 28 and a wider portion 30 located towards the rear of the slot 26. In operation, the front end 20 of the inserted portion 14 is inserted into the wider portion 30 of the slot 26 and the narrow portion 28 of the slot 26 slides in the grooves 24 until the rear of the slot 26 clears the rear end 22 of the inserted portion 14, at which point the blade 18 is fitted in place on the inserted portion 14. When the blade 18 is in its normal position on the inserted portion 14 of the handle 10, the rear end 22 of the inserted portion 14 engages a rear edge 32 of the blade slot 26, which prevents the blade 18 from moving along its slot 26 along the grooves 24 of the inserted portion 14.

In a simple but dangerous maneuver, to remove a blade 18 from the knife handle 10, a nurse will typically use a surgical tool or his or her fingers to disengage the rear edge 32 of the slot 26 of the blade 18 from the rear end 22 of the inserted portion 14 of the handle 10, and then begin sliding the blade slot 26 along the inserted portion 14. This results in an uncontrolled bending of the blade 18 within its elastic limit so that when the inserted portion 14 reaches the wider portion 30 of the slot 26, the blade 18 has a tendency to snap upward. Such bending and sliding of the blade is dangerous because it may cut the nurse. The blade may also be propelled away from the operating area where someone would have to retrieve. The blade may then be lost temporarily. Furthermore, while removing a blade 18 from a handle 10, the nurse's hand may be cut if his or her hand accidentally slips along the blade 18.

Thus, there is a need to facilitate the safe removal and disposal of blades from surgical knife handles. One such attempt to address this problem is the surgical blade removal and disposal device disclosed in U.S. Pat. No. 4,318,473. This patent discloses the use of a blade removing portion which has a guide integral with a case for guiding the handle and its associated blade therethrough. The guide includes a slot deeper than the handle for receiving the handle and for permitting the handle to move downward. The guide also includes a shoulder positionable under the blade for supporting the rear of the blade. When the handle moves downward in the slot, the inserted portion pulls the central portion of the blade down causing it to bow on the shoulder and the forward portion of the case releasing the rear edge of the blade between the blade slot and the handle and permitting the slot of the handle to slide on the inserted portion. The guide also has a stop integral with the case rearward of the shoulder and above the top of the blade prior to bowing the blade for engaging the rear of the blade. The stop also functions to prevent rearward motion of the blade when it is bowed so that the inserted portion moves in the slot to a wider portion of the slot thereby disengaging the blade from the handle. An abutment forward of the guide and integral with the case positioned over the forward portion of the blade and a guard over the rear of the blade prevent the forward and rear portions of the blade from snapping off the case when the blade is disengaged from the inserted portion.

However, this surgical blade removal and disposal device suffers from a number of drawbacks. First, in order to facilitate safe and proper removal of blades, the blade must be placed at a proper angle in the guide means to allow the blade removal operation to take place. Second, the blade must be aligned appropriately within the guide means. Third, although a larger blade may be removed by this surgical blade removal and disposal device, the removal of such large blades requires bending and twisting of the handle and the blade, which is both dangerous and difficult.

In U.S. Pat. No. 5,729,879 discloses a blade removal device with a blade seat for receiving the blade, a handle seat for receiving the handle, a dividing wall provided between the blade seat and the handle seat and having a sharp curved edge for separating the blade from the handle, and a restraining wall for restraining the blade from rearward movement once the blade has been positioned in the blade seat and the handle withdrawn rearwardly. The present inventor has found that his design in this patent needed improved guidance for the handle and blade. The present inventor also found that the entirely rigid device was in some instances difficult to operate to remove a scalpel handle.

In addition to the safe removal and disposal of surgical blades, the surgical staff must maintain strict accountability for all surgical sharps and/or instruments to ensure that none remain in the patient after surgery, or that none of the surgical sharps and/or instruments are lost or lying around the operating room which may cause injury to the unwary. After removal of a blade, it is placed in a disposal unit so that an accounting can be made of the disposed blades and other sharp objects which when added to the unused blades must equal the number of all blades brought into the surgery.

SUMMARY OF THE INVENTION

The present invention is a scalpel blade removal device. This device gives the user a relatively broad opening into which the user inserts the bladed end of the scalpel. The broad opening extends to a sliding ramp, where, after inserting the bladed end into the broad opening, a forward-driven blade edge moves up the sliding ramp. When the user hits the end of the sliding ramp to come to rest on a top ramp, the user merely pulls rearward on the scalpel handle to pull the blade safely free.

More specifically, the invention comprises a broad opening in a sidewall. The sidewall can be located in any convenient location, although a preferred location is a sidewall of a disposable sharps container, as shown in U.S. Pat. No. 5,729,879.

This broad opening is a first blade guide. This first blade guide has generally vertical edges preventing sideways slipping of the blade or handle when a user inserts the bladed end of the scalpel into it. Immediately adjacent to and extending from the broad opening, a narrowing upward ramp is bounded by left and right guide walls.

A broad opening extending to a narrowing upward ramp bounded by left and right guide walls causes the bladed end of a scalpel to be forced from a broad path to a tightly controlled one as the blade edge slides up the upward ramp. The user avoids having to use extreme care to put the scalpel into a relatively narrow path and keep it there. A horizontal top ramp extends from the distal or top end of the upward ramp. An entry to this top ramp is bounded by left and right guide towers.

In the operation of removing a blade from a scalpel handle, a spring loaded notch device is fixed to the left side of the left guide wall. The notch device is adapted to lock behind a proximal end of a scalpel blade as it passes by the notch device on its way up the upward ramp. The blade at this stage is fixed on the scalpel handle, but can be removed quite easily once the notch device locks onto the a scalpel proximal end of a scalpel blade as it passes by the notch device on its way up the upward ramp. Thus, the invention blade remover is simple to operate. Blades are easily removed from scalpel handles in a safe and simple operation.

A sharps container incorporates the removal device, a reinforced latch, a scalpel resting location, and needle cover removers. The sharps container has an upper half and a bottom half connected by three hinges. The upper half and the bottom half are then opened or closed, where the closed position causes a secure latch to keep the container closed. Magnetic sheets line the bottom half for retaining the blades and other sharps. In one form, counting indicia are printed on the magnetic sheets for counting blades and other sharps that are to be disposed. A pad lines the upper half with counting indicia are printed on the pad to count needles and other small sharps.

This disposable sharps container is a unitary, low cost plastic case which sits flat on any surface. Once all the blades have been removed and placed in the sharps container, the sharps container is easily and effectively sealed so that it does not open and expose the blades and/or other sharp objects such as hypodermic needles or suture needles to the environment.

BRIEF DESCRIPTION OF THE DRAWINGS

FIG. 1 is a perspective view of a prior art non-disposable scalpel handle and a disposable blade separated from the handle.

FIG. 2 is a top view of a bottom half of a disposable sharps container box with the invention blade remover incorporated into its side wall and adjacent floor.

FIG. 3 is a perspective and broken away view of the invention blade remover.

FIG. 4 is a top view of the device of FIG. 2 with the notch device in an unflexed position.

FIG. 5 is a cross section 74 view of the device of FIG. 4.

FIG. 8 is the view of FIG. 6 with a scalpel handle and connected blade inserted in the blade remover, with the left side of the scalpel end and blade pressing back the notch device.

FIG. 9 is the device of FIG. 8 with the scalpel handle pulled rearward so that a rearmost edge of the blade is effectively engaged in the notch device.

FIG. 10 is a perspective view of a disposable sharps container with a hinged top and bottom parts of a disposable sharps container with the invention blade remover, hypodermic needle sheath removers, scalpel rests, secure sidewall closures for the openings of the invention blade remover, hypodermic needle sheath removers, and scalpel rests, and secure latch means.

FIG. 11 is a perspective view of a U-shaped part of the hinge of the box of FIG. 10.

FIG. 12 is perspective view of the hinge of the box of FIG. 10.

FIG. 13 is cross section 89 of the latch means of the box of FIG. 10.

FIG. 14 is cross section 87 of the latch means of the box of FIG. 10.

FIG. 15 shows the cross sections of FIGS. 13 and 14 joined in a closed position of the latch means of the box of FIG. 10.

DETAILED DESCRIPTION OF THE INVENTION

Figure 6:
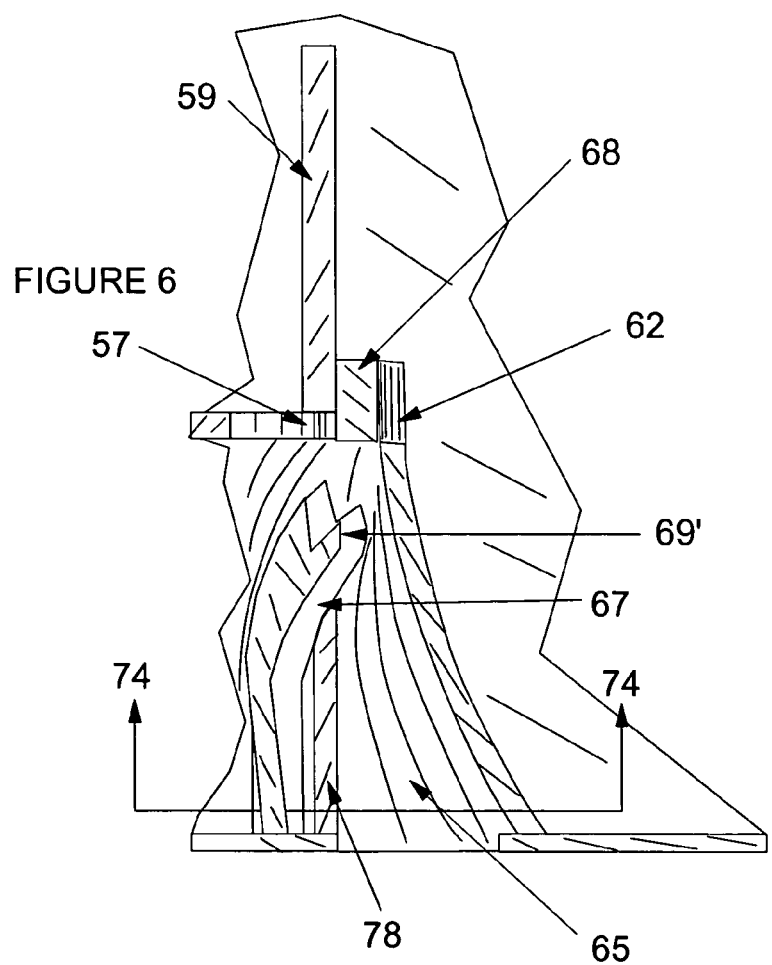
FIG. 6 is a top view of the device of FIG. 2 with the notch device pressed back to receive a back end of a scalpel blade.

The invention is now discussed with reference to the figures.

FIG. 1 shows, as described above, a prior art scalpel handle 12 and blade 18. Section 40 runs along a bottom edge of handle 12 and a mid section of inserted portion 14 and neck portion 16. In FIGS. 8 and 9, section 40 will permit viewing of the operation of the invention blade remover.

FIG. 2 shows a top view of a disposable sharps container 42 with the invention blade remover 50. The blade remover 50 will now be discussed with reference to FIGS. 3 through 7 that show several aspects of blade remover 50.

Blade remover 50 comprises a first blade guide is an opening defined by a bottom of upward ramp 65 and sidewall edges 64 and 72. It is through this opening that the forwardmost part of the bladed end of the scalpel is inserted in a first operating step of the blade remover. A particularly critical aspect of the invention is upward ramp 65. Ramp 65 extends upward from about a 15 to 75 degree angle relative to a floor of a sharps container 42 (FIG. 2). Ramp 65 extends from its lowest and broadest point at the opening forming the first blade guide upward to its highest and narrowest point at its intersection to top ramp 68. In operation, blade edge 34 will slide from the lowest to highest point of ramp 65 and thereafter to rest on top ramp 68.

Upward ramp 65 is bounded on its right side by curved wall 63, where the surface 70 (shown in FIGS. 4 and 5) abuts the right side of blade 18 or scalpel handle 10 as the scalpel is inserted into the invention blade remover. Upward ramp 65 is bounded on its left side in part by a low wall 78, where the surface 66 abuts the blade 18 as the scalpel is inserted into the invention blade remover. Low wall 78 is only part of the guiding means for the blade and scalpel handle as they are inserted into the blade remover. Flexible wall 53 extends inward from an attachment 52 with a sidewall. Attachment 52 is near to edge 72. Flexible wall 53 comprises a surface 51. Flexible wall surface 51 combines with low wall surface 66 to abut a left side of blade 18 or scalpel handle 10 as the scalpel is inserted into the invention blade remover. Flexible wall surface 51 combines with low wall surface 66 to provide as effective guiding means for a left side of the scalpel as surface 70 (shown in FIGS. 4 and 5) provides for the right side of the scalpel.

However, flexible wall 53 serves a more important function than guiding a right side of the scalpel in operation of the blade remover. At the end of flexible wall 53 is notch 56 at short end 55. Notch 56 is the notch that is urged into position behind back end 33 of blade 18 (FIG. 1) that will retain blade 18 in place while scalpel handle 10 is pulled free from blade 18.

Figure 7:
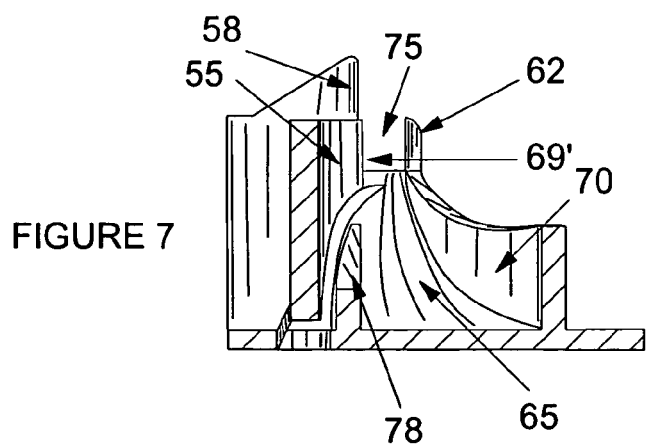
FIG. 7 is a cross section 74 view of the device of FIG. 6.

The structure of flexible wall 53 is unique. At attachment 52, flexible wall 53 has a vertical height of about the height of the sidewall. At short end 55, the vertical height is about from one tenth to about two thirds the vertical height of the sidewall. Cutout 67 extends around the lower periphery of flexible wall 53 except at attachment 52. Thus, flexible wall is free to move in a side to side motion like a tightly spring loaded swinging door. FIGS. 4 and 6 show that distal end 54 can be pressed sideways respectively in directions 69 and 69'. FIG. 4 shows flexible wall 53 in a rest state. FIG. 6 shows flexible wall 53 after it has been pressed left. FIGS. 6 and 7 show the position of flexible wall 53 after a blade and scalpel handle have been inserted into the blade remover. This operation is discussed in more detail with respect to FIGS. 8 and 9.

Flexible wall 53 is cleverly formed during a single molding step with the rest of sharps container box 42 (FIG. 2). The peripheral cutout 67 provides the insertion point for the support wall of the mold for the sides of flexible wall 53.

At the top of upward ramp 65 is top ramp 68. Horizontal top ramp 68 is bounded on the left by edge 58 of lateral extension 57 and a right surface of wall 59. Horizontal top ramp 68 is bounded on the right by a left surface of tower 62. The left and right side boundaries of top ramp 68 continue the guiding means for the blade and scalpel handle as they slide off of the upward ramp 65 and onto top ramp 68.

Operation of the blade remover is now discussed with reference to FIGS. 8 and 9. FIGS. 8 and 9 use a section 40 of scalpel handle 10 with blade 18 (FIG. 1) so that operation of the blade remover is easily seen. FIG. 8 is a view of the operation of the blade remover after:
1. a user holding the handle 10 has inserted the tip of blade 18 into the opening of the first blade guide;
2. the user continues insertion of the scalpel into the blade remover so that edge 34 of blade 18 slides up ramp 65 and almost to top ramp 68;
3. the scalpel has traveled from a broad path at the first blade guide to a narrow path toward the top of upward ramp 65; and
4. in traveling to the narrow path, a left side of the scalpel presses against surface 54 to move flexible wall 53 to the position shown in FIGS. 6 and 7.

FIG. 9 is a view of the operation of the blade remover after:
1. the user continues insertion of the scalpel so the edge 34 of blade 18 rests on top ramp 68;
2. the back end 33 of blade 18 passes by notch 56, whereafter surface 54 springs into contact with neck 16 immediately behind back end 33; and
3. the user pulls back on handle 10 so that back end 33 firmly engages notch 56.

FIG. 9 shows that blade 18 is fixed in the blade remover. The user then continues to pull back on handle 10, causing blade 18 to remain in place as shown in FIG. 9 and eventually disengage from handle 10 entirely. When blade 18 has disengaged from handle 10, blade 18 falls harmlessly along path 82 into the sharps container.

The above blade remover is a dramatic advance in the art. A scalpel is guided from a broad opening to a narrow path that forces the scalpel to push back the notched end of a flexible wall, where the back end of the blade is caught in that notch. Blade removal is a safe and simple operation thereafter.

FIGS. 10 through 15 show a sharps container with a top 83 and bottom 84. Three hinges 85 are formed from U-shaped half 95 on bottom 84 and laterally supported pivot rods 95. Hinges 85 permit top 83 and bottom 84 to be separated. Hinges 85 are operated so that top 83 can close with an almost hermitic seal to bottom 84. Extensions 91 are adapted to closely seal openings for blade remover 92, needle sheath removers 93, and two side be side scalpel rests 94 in bottom 84. The tight sealing of top 83 to bottom 84 prevents any sharps contained in the closed box from being shaken so that a sharp point emerges from the box to harm medical personnel.

Each of the two scalpel rests 94 comprise two aligned notches. One aligned notch is made in box sidewall B and the other aligned notch is in an interior wall A. The notch in sidewall B is aligned with a notch in wall A so that a scalpel with handle and blade can be rest in those notches. A rearward part of the scalpel handle is supported on a bottom edge of the handle in the notch in sidewall B. A more forward part of the scalpel handle and/or its blade are supported at a bottom edge in the notch in wall A. The scalpel rests are extremely important to a surgical procedure. For a long, long time, surgeons and nurses have not had a place to safely and temporarily store a bladed scalpel. If the bladed scalpel is laid down on a surgical tray or on a table top, its straight structure makes is subject to being swept along by movement of gauze or hemostats. That sweeping often means the scalpel ends up on the floor. The present scalpel rests eliminate that risk by providing a place to temporarily store bladed scalpels with other sharps. This temporary storage forces personnel to pay careful attention to a central location for all stored sharps, including needles and blades.

Latch means for the sharps container comprise top extension 86 and bottom receiver 88. Sections 87 and 88 show the latch means in more detail. Top extension 86 comprises a shield box 105 that extends from the sidewalls 102 of top 83. A similar shield box 101 extends from the sidewalls 98 of bottom 84. These shield boxes prevent sharps contained in the closed sharps container to emerge from or harm a person who will re-open the sharps container. FIG. 13 shows that opening 99 is generally made in the sidewall bounded by shield box 101 so edge part 100 forms a generally straight edge for engaging a lip 103' of extension 103 of receiver 88. An opening 106 is formed in sidewalls 102 for molding of extension 103 as attached to the floor edge of top 83. FIG. 15 shows the sharps container of FIG. 10 in a closed position. In a box closing operation, a tip of extension 103 moves past a box edge of receiver 88 until lip 103' springs into engaging connection as shown in FIG. 15. This structure of latch means has proven to be surprisingly effective in preventing opening of the sharps container after dropping or striking with a heavy object.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

We claim:
1. A device unitarily molded into a sharps container adapted to remove a scalpel blade from a scalpel handle, each blade having a rear edge which abuts a rear surface of a neck of the handle in a locking relationship, the handle further having a narrow inserted portion provided at a front end thereof and grooves provided along the periphery of the inserted portion, the blade also having a slot for receiving the grooves of the inserted portion of the handle, the grooves being slidable in the slot and passing through a wider opening at a portion of the slot to permit the blade to be removed from the inserted portion, the device comprising:
   (a) a generally rectangular, vertical and broad opening defined at a bottom edge by a lowest and widest edge of an upward ramp and at left and right edges by edges of, respectively, left and right sidewalls, where the top edge of the broad opening is open;
   (b) the upward ramp extending upward and narrowing backward of the sidewalls from the lowest and widest edge to an uppermost and narrowest edge;

(c) a generally horizontal top ramp extending further back from the uppermost and narrowest edge of the upward ramp, the top ramp having a left to right width about that of the uppermost and narrowest edge of the upward ramp;

(d) a right wall extending up and bounding a right side of the upward ramp;

(e) a left wall bounding a lower part of the left side of the upward ramp;

(f) a flexible wall fixed at one end near a backside of the left sidewall and extending freely therefrom to a notched end, where a right side of the notched end bounds at least part of an upper left part of the upward ramp; and (g) the device is adapted so that:
  (i) a tip of a bladed scalpel may be inserted past the broad opening to force a bottom edge of the blade to slide up the upward ramp and come to rest on the top ramp; and
  (ii) the right side of the notched end springs against the rear surface of the neck of the blade behind the rear edge of the blade, whereafter the handle is withdrawn and the rear edge of the blade is engaged in the notched end.

2. The device of claim 1 wherein the left wall has a substantially lower vertical height than the right wall.

3. The device of claim 2 wherein the flexible wall and the left wall in combination are adapted to prevent slippage to the left of a scalpel inserted into the device.

4. The device of claim 3 wherein the right wall is adapted to prevent slippage to the right of a scalpel inserted into the device.

5. The device of claim 1 wherein the top ramp has a generally rectangular, vertical and narrow opening defined at a bottom edge by a transition of the upward ramp to the top ramp and at left and right edges by edges of, respectively, left and right top towers, where the top edge of the narrow opening is open.

6. The device of claim 5 wherein the left wall has a substantially lower vertical height than the right wall.

7. The device of claim 1 wherein the flexible wall has a greatest vertical height at its attachment and narrows to a smallest vertical height at the notched end.

8. A device adapted to remove a scalpel blade from a scalpel handle, each blade having a rear edge which abuts a rear surface of a neck of the handle in a locking relationship, the device comprising:

(a) a broad opening defined at a bottom edge by a lowest and widest edge of an upward ramp and at left and right edges by edges of, respectively, left and right sidewalls, where the top edge of the broad opening is open;

(b) the upward ramp extending upward and narrowing backward of the sidewalls from the lowest and widest edge to an uppermost and narrowest edge;

(c) a right wall extending up and bounding a right side of the upward ramp;

(d) a left wall bounding a lower part of the left side of the upward ramp;

(e) a flexible wall fixed at one end and extending freely therefrom to a notched end, where a right side of the notched end bounds at least part of an upper left part of the upward ramp; and (f) the device is adapted so that:
  (i) a tip of a bladed scalpel may be inserted past the broad opening to force a bottom edge of the blade to slide up the upward ramp; and
  (ii) the right side of the notched end springs against the rear surface of the neck of the blade behind the rear edge of the blade, whereafter the handle is withdrawn and the rear edge of the blade is engaged in the notched end.

9. The device of claim 8 wherein a generally horizontal top ramp extends further back from the uppermost and narrowest edge of the upward ramp, the top ramp having a left to right width about that of the uppermost and narrowest edge of the upward ramp.

10. The device of claim 8 wherein the left wall has a substantially lower vertical height than the right wall.

11. The device of claim 8 wherein the flexible wall is fixed at one end near a backside of the left sidewall and extends freely therefrom to the notched end.

* * * * *